US007660383B2

(12) United States Patent
Sakaguchi et al.

(10) Patent No.: US 7,660,383 B2
(45) Date of Patent: Feb. 9, 2010

(54) THREE DIMENSIONAL IMAGE PROCESSING APPARATUS AND X-RAY DIAGNOSIS APPARATUS

(75) Inventors: Takuya Sakaguchi, Shioya-gun (JP);
Michael D. Silver, Northbrook, IL (US);
Jingwu Yao, Wheeling, IL (US); Mei
Chen, Elk Grove Village, IL (US);
Stefan Bozhilov, LomBard, IL (US);
Satoru Ohishi, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 342 days.

(21) Appl. No.: 11/844,048

(22) Filed: Aug. 23, 2007

(65) Prior Publication Data

US 2009/0052613 A1    Feb. 26, 2009

(51) Int. Cl.
*A61B 6/00* (2006.01)
(52) U.S. Cl. ......................................................... 378/8
(58) Field of Classification Search ..................... 378/4, 378/8
See application file for complete search history.

(56) References Cited

U.S. PATENT DOCUMENTS

| | | | | |
|---|---|---|---|---|
| 6,196,715 | B1 * | 3/2001 | Nambu et al. | 378/197 |
| 6,424,731 | B1 * | 7/2002 | Launay et al. | 382/128 |
| 6,501,848 | B1 * | 12/2002 | Carroll et al. | 382/128 |
| 7,187,746 | B2 | 3/2007 | Sakaguchi et al. | |
| 2002/0181645 | A1 * | 12/2002 | Bruder et al. | 378/8 |
| 2004/0175024 | A1 * | 9/2004 | Rasche et al. | 382/128 |
| 2005/0069081 | A1 * | 3/2005 | Kokubun et al. | 378/15 |
| 2005/0220264 | A1 | 10/2005 | Homegger | |
| 2005/0226485 | A1 | 10/2005 | Boese | |
| 2006/0285632 | A1 * | 12/2006 | Boese et al. | 378/8 |

OTHER PUBLICATIONS

U.S. Appl. No. 11/608,005, filed Dec. 7, 2006, Takuya Sakaguchi, et al.
U.S. Appl. No. 11/680,122, filed Feb. 28, 2007, Takuya Sakaguchi.
B. Movassaghi, et al., "3D coronary reconstruction from calibrated motion-compensated 2D projections based on semi-automated feature point detection," Proceedings of SPIE, vol. 5370, 2004, pp. 1943-1950.

* cited by examiner

*Primary Examiner*—Edward J Glick
*Assistant Examiner*—Alexander H Taningco
(74) *Attorney, Agent, or Firm*—Oblon, Spivak, McClelland, Maier & Neustadt, L.L.P.

(57) ABSTRACT

A three dimensional image processing apparatus includes a storage unit storing data of images in different radiographing directions together with information concerning cardiac phases, a key image selection unit selecting key images from the images, a feature point designation unit designatting feature points on the selected key images in accordance with operation by an operator, and an image reconstruction unit reconstructing a three dimensional image from the images on the basis of positions of the designated feature points, wherein the key image selection unit selects, as the key images, a pair of images which are located at the same cardiac phase and whose radiographing directions are different by a substantially predetermined angle and images spaced apart from each other by an angle obtained by substantially equally dividing an interval between the pair of images by a predetermined number.

30 Claims, 12 Drawing Sheets

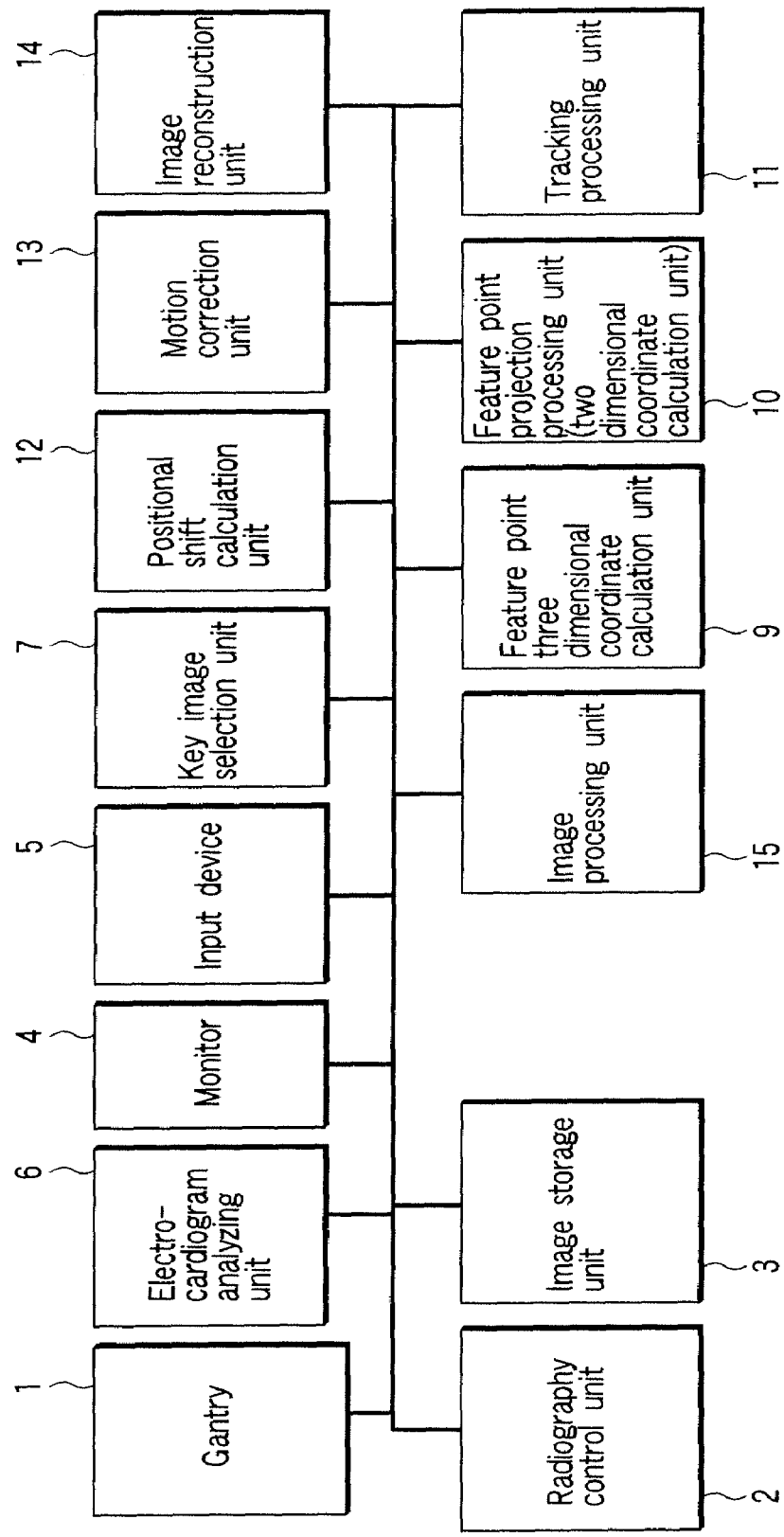
F I G. 2

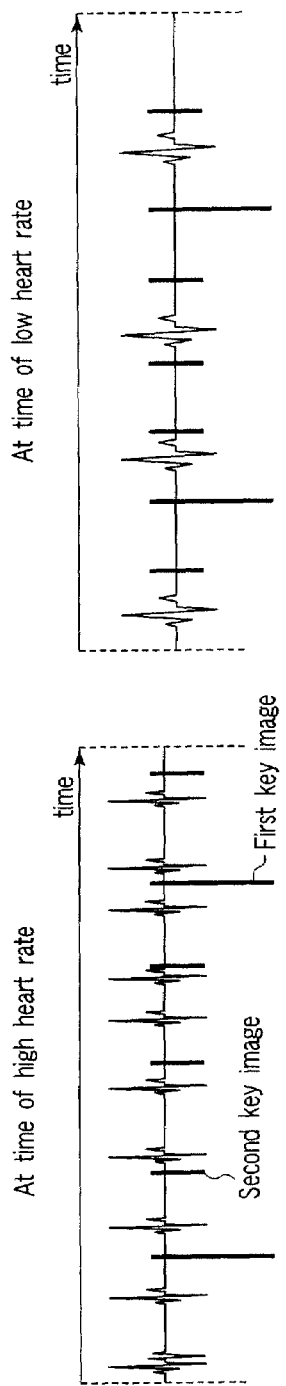
F I G. 8A
F I G. 8B
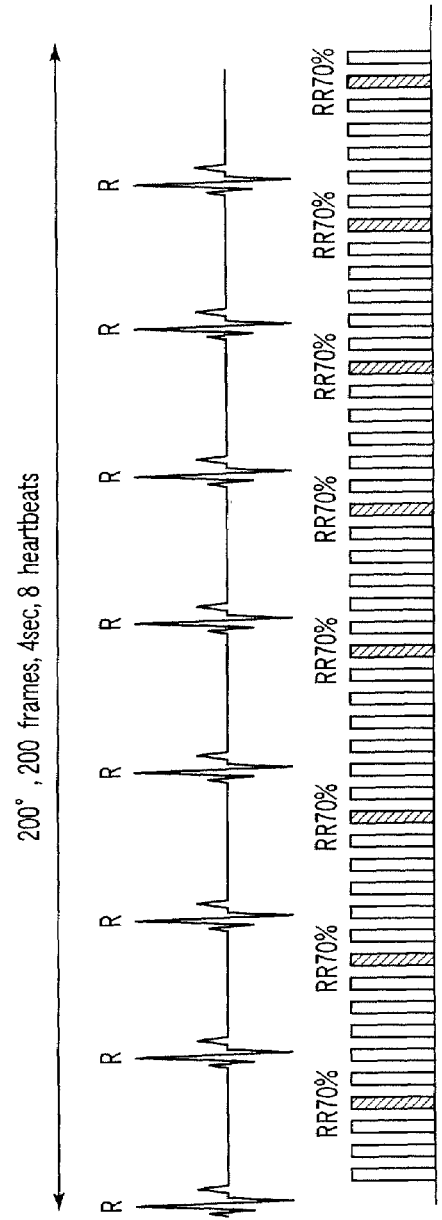
F I G. 9

No key images are automatically selected in heartbeat with arrhythmia

Many key images are automatically selected in heartbeat with arrhythmia

THREE DIMENSIONAL IMAGE PROCESSING APPARATUS AND X-RAY DIAGNOSIS APPARATUS

BACKGROUND OF THE INVENTION

1. Field of the Invention

The present invention relates to a three dimensional image processing apparatus which reconstructs a three dimensional image from a plurality of X-ray images obtained in different radiographing directions.

2. Description of the Related Art

Three dimensional image reconstruction processing is to be performed for a moving object, more specifically, for example, a cardiovascular vessel. Since the cardiovascular vessel moves, reconstructing its image by a conventional technique causes a large motion blur. The image quality of the reconstructed image is unsuitable for diagnosis. There have been proposed several countermeasure techniques for such a problem. For example, the position of a region on an image is corrected, and a three dimensional image is reconstructed from the corrected image.

This technique generates, for example, 200 images at different radiography angles. The operator selects several discrete key images from the 200 images. The operator manually designates anatomically characteristic regions (feature points) on the several key images. The system calculates the three dimensional coordinates of the feature points by geometric calculation from the designated feature points and the radiography angles. The system re-projects the three dimensional coordinates on the respective images the system also tracks the feature points for non-selected frames. The system corrects the shifts between the re-projected positions and the tracked positions.

This makes it possible to perform reconstruction processing upon performing image deformation to make the image look like stationary. The obtained reconstructed image is therefore a sharp image without any motion blur.

However, the operation which the operator performs to designate feature points accompanies arbitrariness. This arbitrariness makes the image quality of a reconstructed image unstable.

As shown in FIG. 1, for example, when images are disproportionally selected, numbers of frames NA, NB, and ND greatly vary. The tracking accuracy in the interval A is relatively low because number of tracking frames are large, and the tracking accuracy in the interval D is relatively high because number of tracking frames are small. The accuracy of position correction is low in the interval A, and the accuracy of position correction is high in the interval B. This degrades the image quality of a final reconstructed image. That is, the image quality of reconstructed images becomes unstable in accordance with the selection of images.

BRIEF SUMMARY OF THE INVENTION

It is an object of the present invention to stabilize the image quality of a reconstructed image by suppressing variations in tracking interval length.

According to a first aspect of the present invention, there is provided a three dimensional image processing apparatus comprising: a storage unit which stores data of a plurality of images in different radiographing directions together with information concerning cardiac phases; a key image selection unit which selects a plurality of key images from the plurality of images; a feature point designation unit which designates feature points on the selected key images in accordance with operation by an operator; and an image reconstruction unit which reconstructs a three dimensional image from the plurality of images on the basis of positions of the designated feature points, wherein the key image selection unit selects, as the key images, a pair of images which are located at the same cardiac phase and whose radiographing directions are different by a substantially predetermined angle and a plurality of images spaced apart from each other by an angle obtained by substantially equally dividing an interval between the pair of images by a predetermined number.

According to a second aspect of the present invention, there is provided a three dimensional image processing apparatus comprising: a storage unit which stores data of a plurality of images in different radiographing directions together with information concerning cardiac phases; a key image selection unit which selects a plurality of key images from said plurality of images; a feature point designation unit which designates feature points on the selected key images in accordance with operation by an operator; and an image reconstruction unit which reconstructs a three dimensional image from said plurality of images on the basis of positions of the designated feature points, wherein the key image selection unit selects the key images at a rate of two images per heartbeat when a heart rate is not more than a first threshold, and selects the key images at a rate of one image per heartbeat when a heart rate is higher than the first threshold.

According to a third aspect of the present invention, there is provided a three dimensional image processing apparatus comprising: a storage unit which stores data of a plurality of images in different radiographing directions together with information concerning cardiac phases; a key image selection unit which selects a plurality of key images from said plurality of images; a feature point designation unit which designates feature points on the selected key images in accordance with operation by an operator; and an image reconstruction unit which reconstructs a three dimensional image from said plurality of images on the basis of positions of the designated feature points, wherein the key image selection unit selects the key images so that a ratio of image number of the selected key images to a heartbeat number when frequency of heartbeats are higher than a first threshold is lower than the ratio when frequency of heartbeats are not higher than the first threshold.

According to a fourth aspect of the present invention, there is provided a three dimensional image processing apparatus comprising: a storage unit which stores data of a plurality of images in different radiographing directions together with information concerning cardiac phases; a key image selection unit which selects a plurality of key images from said plurality of images; a feature point designation unit which designates feature points on the selected key images in accordance with operation by an operator; and an image reconstruction unit which reconstructs a three dimensional image from said plurality of images on the basis of positions of the designated feature points, wherein the key image selection unit selects the key images at a rate of one image per heartbeat when a heart beat is not more than a first threshold, and selects the key images at a rate of one image per heart beats when a heart rate is more than the first threshold.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the preferred embodiments given below, serve to explain the principles of the invention.

FIG. 2 is a block diagram showing the arrangement of a three dimensional image processing apparatus of an embodiment;

FIG. 8A is an exemplary view showing a tracking interval length at a high heart rate in FIG. 7;

FIG. 8B is an exemplary view showing a tracking interval length at a low heart rate in FIG. 7;

FIG. 9 is a supplementary view for explaining a second technique for key image selection processing in step S2 in FIG. 4;

DETAILED DESCRIPTION OF THE INVENTION

A three dimensional image processing apparatus according to an embodiment of the present invention will be described below with reference to the views of the accompanying drawing. The three dimensional image processing apparatus will be described as an apparatus incorporated in an X-ray system. Obviously, however, this apparatus may be singly used. Prior to a description, the terms used will be defined as follows:

X-ray system: a C-arm type apparatus. In this system, an X-ray source faces a detector, which are supported by a C-arm. The C-arm simultaneously rotates the X-ray source and the detector while they face each other. In rotational radiography performed by the X-ray system, the C-arm rotates slowly (50 deg/sec) in contrast to the rotation of the gantry in CT (900 deg/sec). For this reason, to take 200° information necessary for reconstruction 5 second is required. When a moving object such as the heart is to be reconstructed, the movement of the object cannot be neglected.

rotational radiography: a radiographing method of radiographing a subject at, for example, a rate of one image/degree while rotating around the subject.

tracking: searching for, when a small area of about 31×31 is set on the Nth image, the most similar region in the adjacent (N+1)th image in a state wherein, for example, there are a plurality of images of 1024×1024 two dimensional images and a subject depicted in the images hardly moves between the images. Repeating this operation can obtain the movement locus of the initially set small area. As similarity calculation methods, the following calculation methods are known: Sum of square distance, Sum of square distance, a cross-correlation method, or Mutual information.

feature point or feature pattern: a pattern discriminated as a feature on an image, more specifically, for example, a blood vessel branch portion, stricture portion, or stent marker.

feature point designating operation: the operation of moving a mouse cursor on an image displayed on the screen and clicking the mouse.

image: One image of consecutive still images and synonymous with "image" in the description.

R-R interval: the interval (time) between R waves of an electrocardiogram signal.

cardiac phase: expressed by 0 to 100% by equally dividing the time interval between an R wave and the next R wave of an electrocardiogram signal by 100. For example, RR70% represents a position which is located within the interval between an R wave and the next R wave and away from the preceding R wave by a distance (time) of 70% of the interval from the preceding R wave.

same cardiac phase: images, of the image data acquired throughout a plurality of heartbeats, which are located at the same cardiac phase. Image data are acquired discretely. In the strict sense, therefore, it is very unlikely that images at the same cardiac phase can be obtained. In practice, "same cardiac phase" indicates images located at almost the same cardiac phase.

Figure 1:
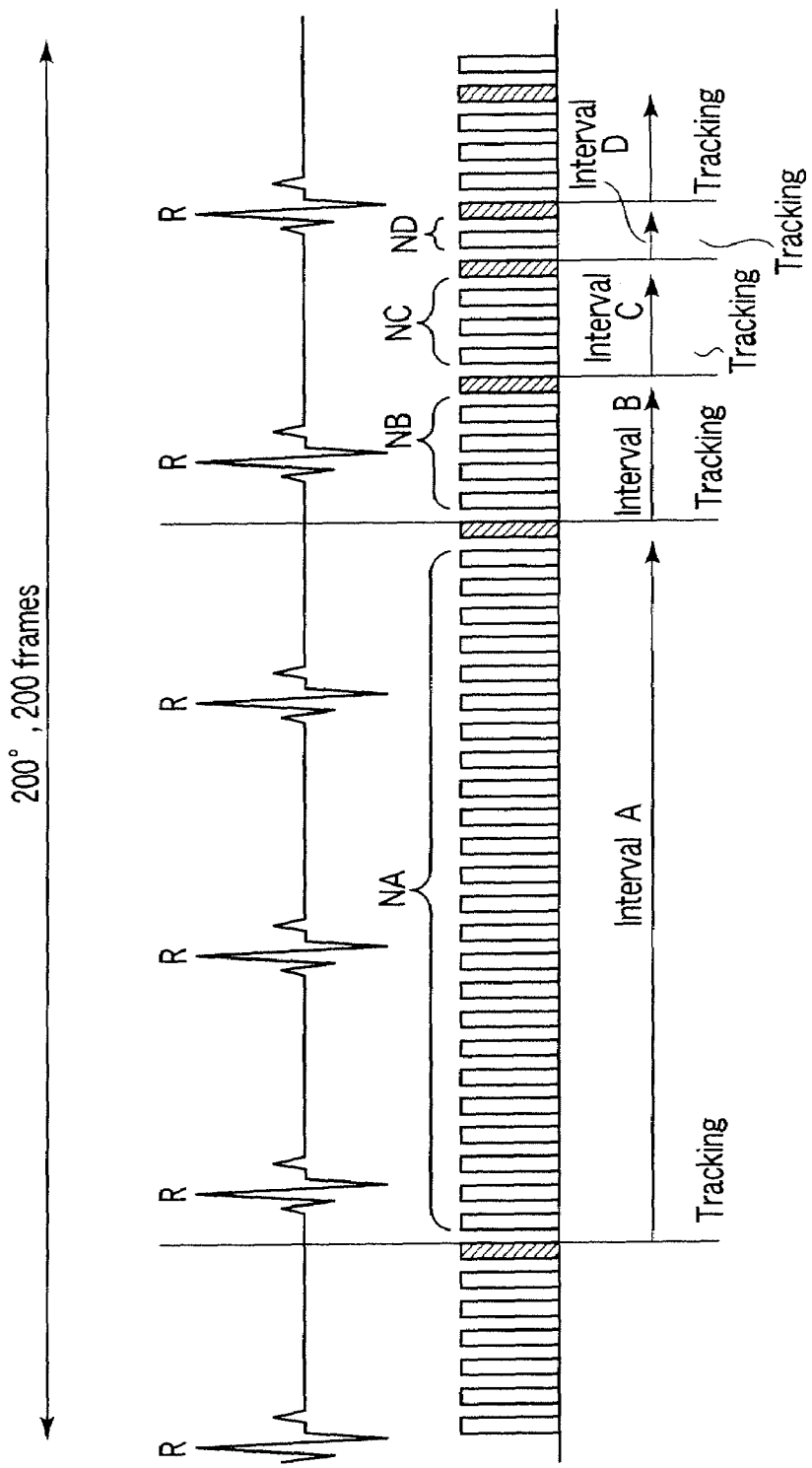
FIG. 1 is a view showing the unstability of tracking interval lengths in the prior art.
Figure 3:
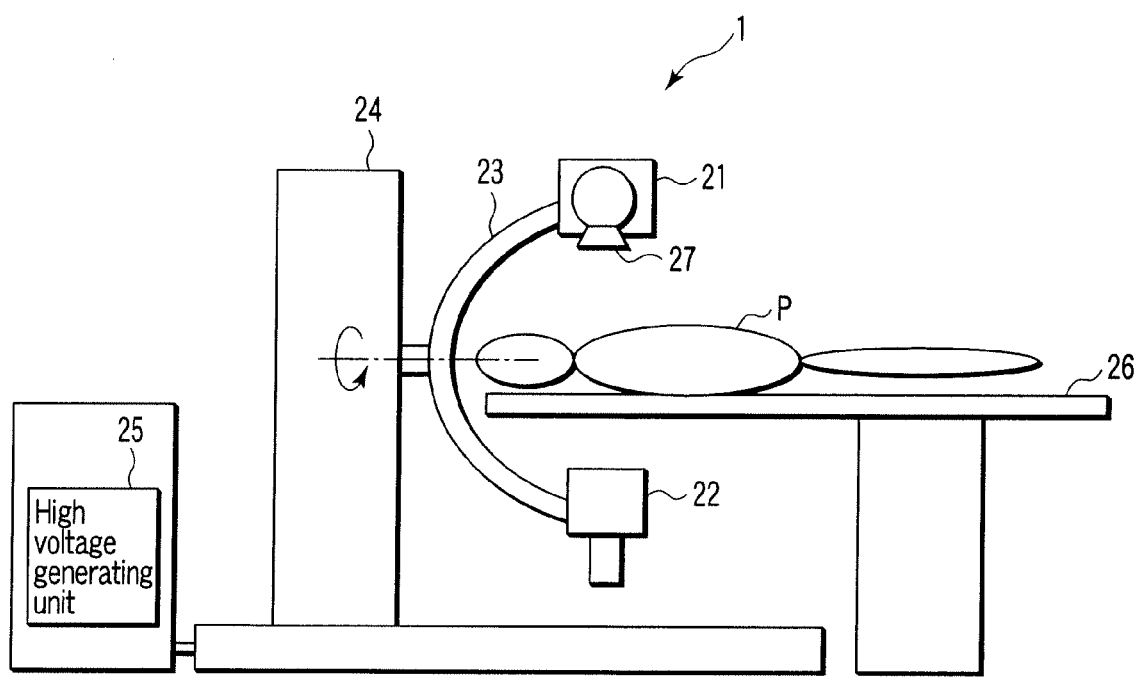
FIG. 3 is a view showing the structure of a gantry in FIG. 2.

FIG. 2 shows a radiographic apparatus incorporating a three dimensional image processing apparatus according to this embodiment. As shown in FIG. 3, a gantry 1 includes an X-ray tube 21 and an X-ray detector 22. A high voltage generating unit 25 generates a high voltage to be applied between the electrodes of the X-ray tube 21 and also generates a filament current to be supplied to the cathode filament of the X-ray tube 21. Upon receiving the high voltage and filament current, the X-ray tube 21 generates X-rays. The X-ray detector 22 is typically a solid flat panel detector comprising a two dimensional array of a plurality of detection elements (pixels) which directly or indirectly convert incident X-rays into electric charges. The X-ray tube 21 is mounted on, for example, one end of a floor type C-arm 23. The X-ray detector 22 is mounted on the other end of the C-arm 23. The X-ray detector 22 faces the X-ray tube 21 through a subject P placed on a bed 26. The C-arm 23 is rotatably supported on a stand 24. Repeating radiography while rotating the C-arm 23 makes it possible to acquire X-ray images (transmission images) in many directions which are required for three dimensional image reconstruction.

A radiography control unit 2 controls the application of high voltages from the high voltage generating unit 25 to the X-ray tube 21 and reading of signals from the X-ray detector 22 in order to execute rotational radiography and generate X-ray image (projection image) data. This apparatus includes an image storage unit 3 to store this X-ray image data.

Although not shown, an electrocardiograph is attached to the subject P to acquire the electrocardiograms of the subject P. An electrocardiogram analyzing unit 6 identifies a cardiac phase when an X-ray image is captured from an electrocardiogram. A cardiac phase represents a time point between R waves, and is generally expressed in percentage. The data of a cardiac phase at the time of radiography is associated with each X-ray image. The apparatus includes an image reconstruction unit 14 for reconstructing three dimensional image data from X-ray images in many directions which are stored in the image storage unit 3.

A system for correcting the positional shift of a subject image in the image coordinate system between X-ray images in many directions due to respiration, cardiac beats, and the like comprises a monitor 4 for displaying X-ray images, an input device 5 for feature point designating operation and the like, a key image selection unit 7, a feature point three dimensional coordinate calculation unit 9, a feature point projection processing unit 10, a feature point extraction unit (tracking unit) 11, a positional shift calculation unit 12, a motion correction unit 13, and an image processing unit 15.

The key image selection unit 7 selects X-ray images (to be referred to as key images) from plurality of X-ray images in many directions which are stored in the image storage unit 3. A key image is a specific image for making the operator manually designate a feature point. Key image selection processing will be described in detail later.

Figure 5:
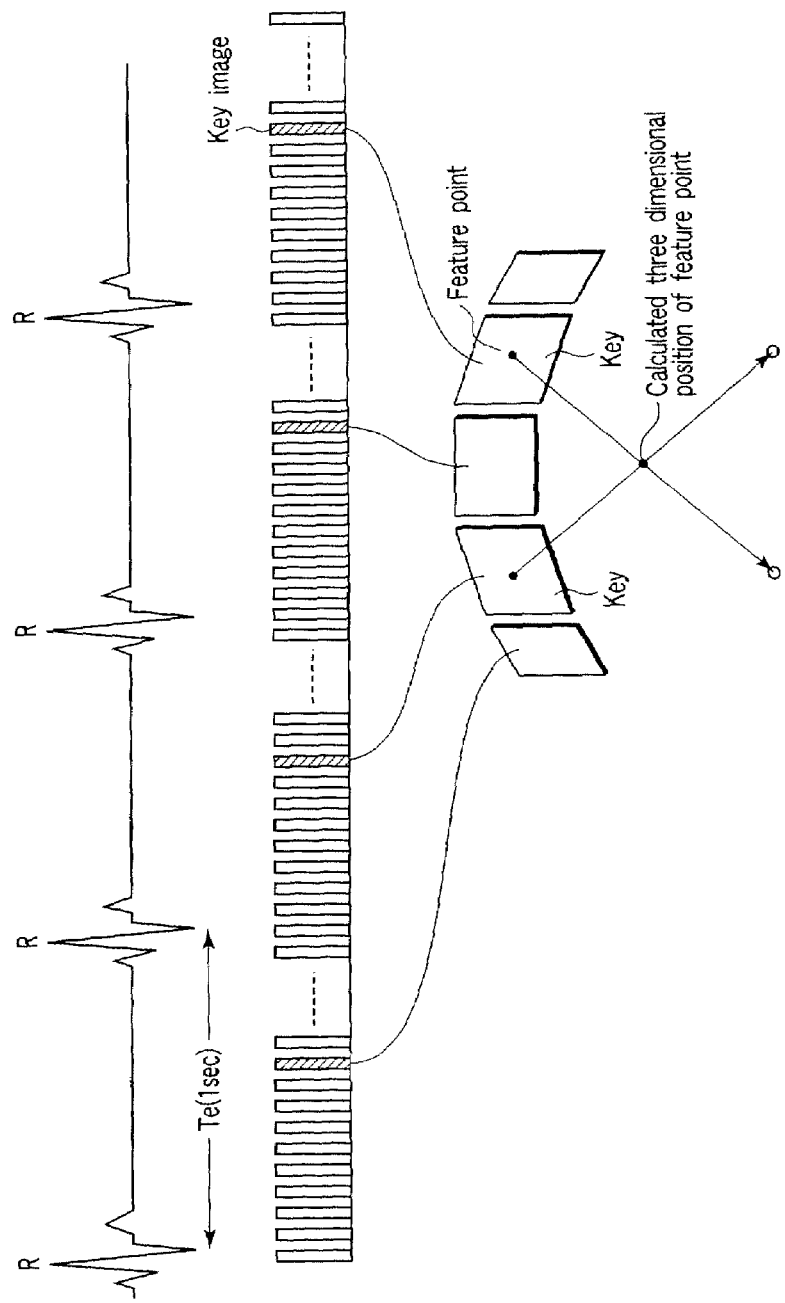
FIG. 5 is a supplementary view for explaining feature point back projection processing in step S4 in FIG. 4.

As shown in FIG. 5, the feature point three dimensional coordinate calculation unit 9 calculates the three dimensional coordinates (three dimensional position) of a feature point by geometric calculation on the basis of the two dimensional coordinates of a plurality of feature points designated on a pair of key images (first key images as described later) and the respective radiographing directions. The feature point projection processing unit 10 calculates the two dimensional coordinates of a feature point projected on each non-key image on the basis of the calculated three dimensional coordinates of the feature point and the radiographing directions of the remaining images (non-key images) other than the key images. The feature point tracking unit 11 tracks the feature point on each non-key image in accordance with the radiographing order starting with a feature point designated on a key image being a base point.

Figure 4:
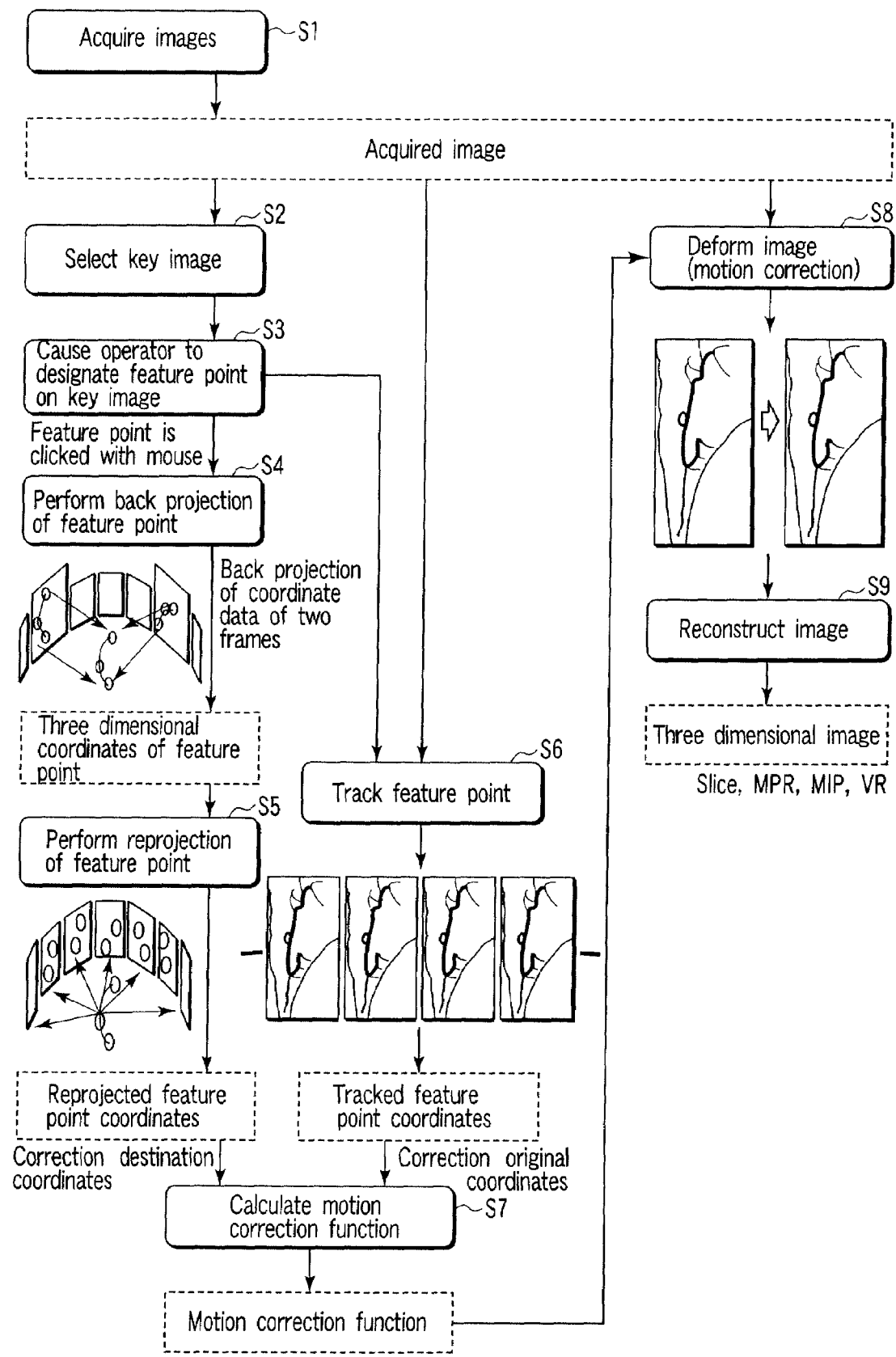
FIG. 4 is a view schematically showing the overall operation of this embodiment.

The positional shift calculation unit 12 calculates the positional shifts of the two dimensional coordinates of the feature points tracked by the feature point tracking unit 11 with respective to the two dimensional coordinates of the feature points calculated by the feature point projection processing unit 10 for each image. The motion correction unit 13 corrects the positions of the non-key images in accordance with the positional shifts calculated by the positional shift calculation unit 12. The image reconstruction unit 14 reconstructs three dimensional image data on the basis of the key images and the position-corrected non-key images FIG. 4 shows an outline of the overall operation between image acquisition and the generation of a three dimensional image in this embodiment. The C-arm 23 continuously rotates under the control of the radiography control unit 2, and radiography is repeated during this period. For example, the C-arm 23 rotates at a rate of 50°/sec. With this operation, the apparatus acquires the data of a plurality of X-ray images in different radiographing directions, and stores the data in the image storage unit 3 in association with the radiographing directions (S1). For example, while the C-arm 23 rotates through 200° in four sec, the apparatus acquires 200 X-ray images.

The key image selection unit 7 selects, for example, key images of eight images from the 200 X-ray images (S2).

A feature point support unit 8 sequentially displays the key images on a monitor 4 image by image in accordance with the radiographing order, and feature points are designated on the respective key images in accordance with the designating operation on the input device 5 by the operator (S3). This apparatus uses, as feature points, relatively identifiable markers in anatomical (morphological) terms, e.g., blood vessel branch portions, stricture portions, and stent markers.

When the designation of feature points on all the key images is complete, the feature point three dimensional coordinate calculation unit 9 calculates the three dimensional coordinates of the feature points (S4). The apparatus then calculates the two dimensional coordinates of feature points on the remaining non-key images other than the key images, on which feature points are projected, by re-projection processing on the basis of the calculated three dimensional coordinates of the feature points and the radiographing directions of the non-key images (S5). The two dimensional coordinates of these feature points will be referred to as the calculated two dimensional coordinates of the feature points.

Figure 6:
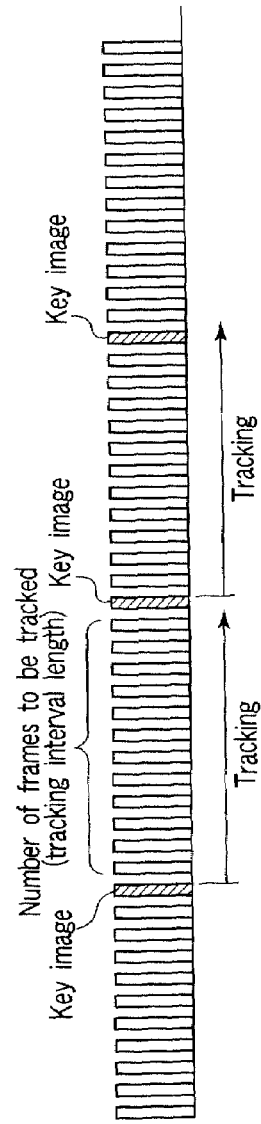
FIG. 6 is a supplementary view for explaining feature point tracking processing in step S6 in FIG. 4.

As shown in FIG. 6, with a designated feature point on a key image being a base point, this apparatus sequentially tracks feature points on a plurality of non-key images immediately before the next key image (S6). Relatively high tracking accuracy is obtained from a relatively small number of images tracked (a relatively short tracking interval length). Relatively low tracking accuracy is obtained from a relatively large number of images tracked (a relatively long tracking interval length). The operation load on the operator when designating feature points is heavy when the number of images tracked is relatively large, and vice versa.

The two dimensional coordinates of the tracked feature points will be referred to as the actual two dimensional coordinates of the feature points to discriminate them from the calculated two dimensional coordinates of the feature points. Assume that a subject image depicted on an image hardly moves between images, and, for example, a small area of about 31×31 is set as a feature point on the image of the Nth key image. In this case, tracking processing is the processing of searching for the most morphologically similar area in the non-key image of the adjacent (N+1)th image. Sequentially repeating this processing in accordance with the radiographing order makes it possible to obtain the movement locus of the feature point in the initially set small area (tracking). As a similarity calculation method, this apparatus may arbitrarily use a known calculation method such as Sum of square distance, Sum of square distance, a cross-correlation method, or Mutual information.

The positional shift calculation unit 12 calculates the positional shifts of the actual two dimensional coordinates of the feature points with respect to the calculated two dimensional coordinates of the feature points as motion correction functions (S7). The positions of the non-key images are corrected on the basis of the calculated positional shifts (S8), and the data of a three dimensional image is reconstructed on the basis of the corrected non-key images and the key images (S9). The image processing unit 15 then renders the data and displays the resultant image on the monitor 4.

(First Technique for Key Image Selection Processing)

Figure 7:
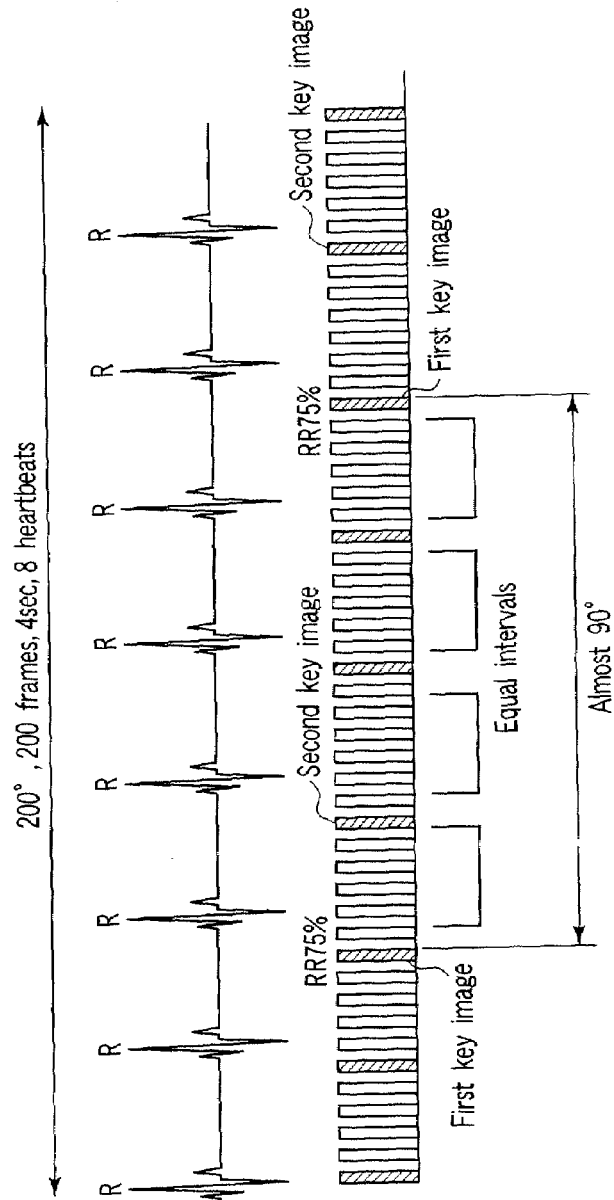
FIG. 7 is a supplementary view for explaining a first technique for key image selection processing in step S2 in FIG. 4.

As shown in FIG. 7, the apparatus selects, as images serving as base points, a pair of X-ray images (first key images) at the same cardiac phase and at radiography angles most approximate to 90° from a plurality of X-ray images. The apparatus selects, as second key images, a plurality of images spaced apart at angles obtained by almost equally dividing the angle difference between the radiography angle of one first key image and the radiography angle of the other first key image by a predetermined number. The apparatus outputs the first and second key images as key images.

More specifically, first of all, the apparatus selects, as first key images, a pair of images which have a radiography angle difference of about 90° and are located at the same cardiac phase. The apparatus then selects, as second key images, images radiographed at angles obtained by almost equally dividing the angle difference between the selected pair of first key images. For example, second key images are selected at intervals of 22° so as to divide the angle difference between the pair of first key images into four parts. The apparatus also selects second key images at intervals of 22° outside the pair of first key images as base points. With this operation, a total of nine key images as first and second key images are automatically selected from the 200 images. The nine key images obtained in this manner are sequentially displayed on the monitor. The operator designates feature points on the respective nine key images.

The cardiac phases of the first pair of first key images need to be equivalent to each other. Typically, the three dimensional coordinates (three dimensional positions) of the feature points are calculated by geometric calculation from the two dimensional coordinates of the designated feature points on the pair of first key images and the radiographing directions of the pair of first key images. The feature point projection processing unit 10 calculates the two dimensional coordinates of the feature points projected on the respective non-key images on the basis of the calculated three dimensional coordinates of the feature points and the radiographing directions of the remaining images (non-key images) other than the key images. The feature point tracking unit 11 tracks the feature points on the non-key images with the feature points designated on the key images being base points.

The first technique can solve the conventional problem that since images are selected at the same cardiac phase, the number of images designated increases at the time of a high heart rate to result in requiring more labor, and the interval increases at the time of a low heart rate to result in deterioration in performance, thus making the final image quality unstable. That is, according to this technique, since key images are selected at equal intervals, the tracking interval length does not depend on the heart rate and becomes stable. This stabilizes the tracking accuracy and final image quality. In addition, since key images are selected at equal intervals, the operation load on the operator does not vary. Furthermore, since the tracking interval length is always constant, tracking results tend to be stable.

(Second Technique for Key Image Selection Processing)

In the second technique, images are automatically selected at the same cardiac phase. When the heart rate is relatively low, a plurality of images are selected per heartbeat. When the heart rate is relatively high, one image is selected per heartbeat or a plurality of heartbeats.

The X-ray tube 21 and the X-ray detector 22 rotate around the subject. For example, they rotate about 200°. When, for example, a radiographic system is driven at a rate of 50 images/sec and a support device is rotated at 50 deg/sec, the radiography time is 200 deg÷50 deg/sec=4 sec, and the number of images radiographed is 4 sec×50 images/sec=200 images. At this time, if the heart rate of the subject is 120 beats/min, eight heartbeats occur during radiography.

In a steady state wherein the heart rate is higher than 75 beats/min and equal to or lower than 150 beats/min, as shown in FIG. 9, the same cardiac phase is specified from each heartbeat, and images are automatically selected at a rate of one image/heartbeat. With this operation, eight images are automatically selected from 200 images. A cardiac phase is preset in advance. If, for example, the preset value is RR70%, images nearest to RR70% are selected from the respective heartbeats.

In a state wherein the heart rate is 75 beats/min or less, two cardiac phases are specified from each heartbeat, and images at the two cardiac phases are automatically selected per heartbeat. This makes it possible to suppress a deterioration in tracking accuracy. That is, if key images are selected in a low heart rate state at the same frequency as that in a steady state, the number of key images become extremely small, resulting in a very long tracking interval length. Consequently, the tracking accuracy deteriorates. This technique can suppress such a deterioration in tracking accuracy.

If, for example, the heart rate is 40 beats/min, only 2.6 heartbeats occur during radiography. In this case, only two or three images are selected. Selecting only two or three key images will increase the tracking interval length. This may cause an extreme deterioration in tracking accuracy. If, therefore, the heart rate is extremely low (e.g., 75 beats/min or less), another cardiac phase is set in addition to a preset cardiac phase to automatically select two key images per heartbeat. More specifically, if RR70% is preset, RR20% is added to select five images even with respect to a patient with 40 beats/min.

In a state wherein the heart rate is higher than 150 beats/min, if key images are selected at the same frequency as that in a steady state, the number of key images selected becomes extremely large. In this case, this technique automatically thin out key images to be selected.

If, for example, the heart rate is 240 beats/min, 16 heart beats occur during radiography, and 16 images are automatically selected. If the tracking performance remains the same regardless of whether the number of images selected is 16 or 8, selecting 16 images will increase the load on the operator but does not contribute to any improvement in image quality. In this case, therefore, this apparatus automatically select one image per two heartbeats instead of one image per heartbeat. More specifically, if the heart rate is, for example, 240 beats/min, eight images are automatically selected. This can reduce the load on the operator without any deterioration in image quality.

Figure 10A:
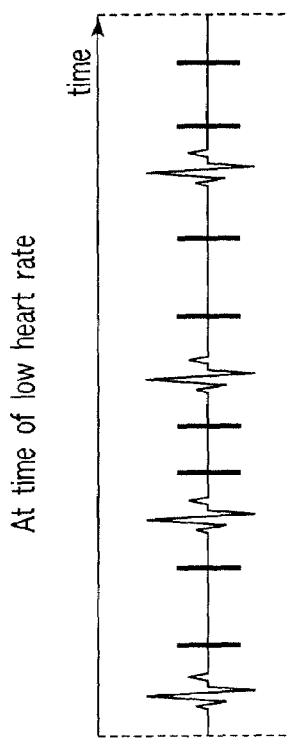
FIG. 10A is an exemplary view showing a tracking interval length at a high heart rate in FIG. 9.
Figure 10B:
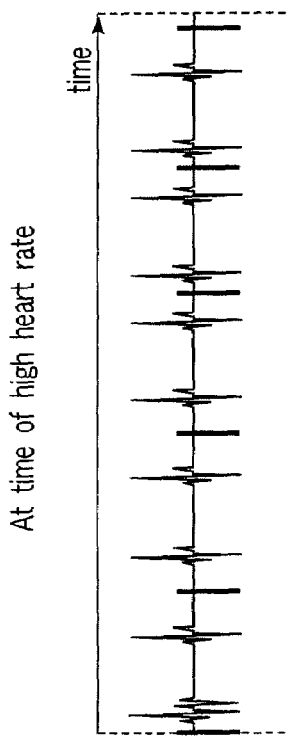
FIG. 10B is an exemplary view showing a tracking interval length at a low heart rate in FIG. 9.

As described above, according to this technique, as shown in FIGS. 10A and 10B, since the tracking interval length does not much depend on the heart rate and is relatively stable, the tracking accuracy is relatively stable, and the final image quality is relatively stable. In addition, since key images are selected at equal intervals, the operation load on the operator does not vary. Furthermore, since the tracking interval length is always constant, tracking results tend to be stable.

In addition, in this technique, since the same cardiac phase is selected, the shape of the heart remains almost the same. Therefore, the influence of deformation accompanying heartbeats is small on the selection of feature points. This allows the operator to easily designate feature points. Furthermore, since selected key images are at the same cardiac phase, the three dimensional coordinates of a feature point can be calculated by using two arbitrary images of the selected key images. The calculation to be performed is not limited to the calculation of the three dimensional coordinates of a feature point by using two images, and the three dimensional coordinates of a feature point can be calculated by using three or more images. In this case, since the calculated three dimensional coordinates are the average values of many key images, three dimensional coordinate calculation increases in stability (even large noise in one image is suppressed by other images).

(Third Technique for Key Image Selection Processing)

This technique adds key images if a tracking result is not good.

Figure 11:
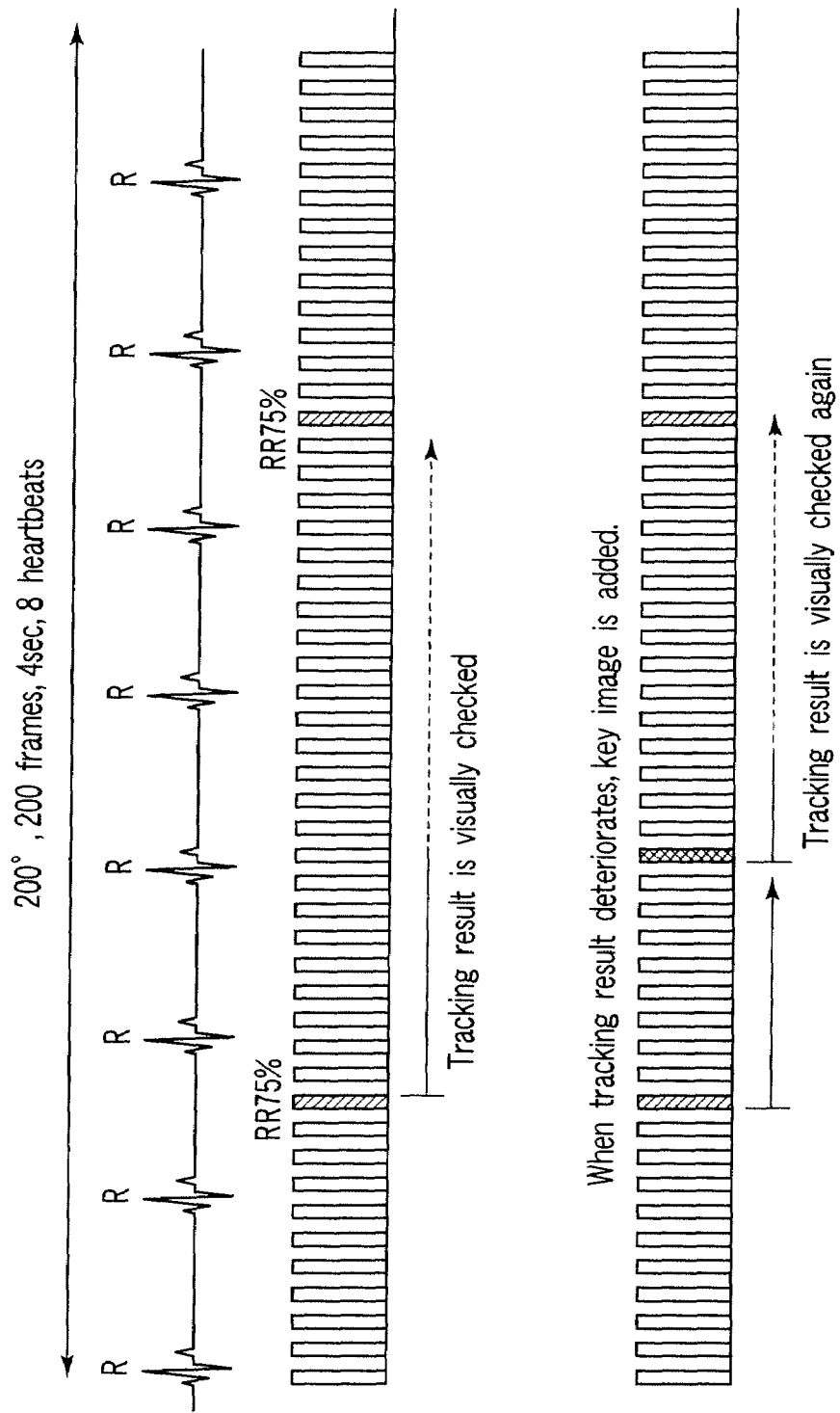
FIG. 11 is a supplementary view for explaining a third technique for the key image selection processing in step S2 in FIG. 4.

This technique selects, as key images, a pair of images which are located at the same cardiac phase and have a radiography angle difference of about 90°. The operator designates feature points on this pair of key images. As shown in FIG. 11, the apparatus then performs tracking processing with the feature points designated on the key image being base points. The apparatus sequentially displays tracking results on the screen image by image. The operator visually checks the screen to monitor whether the automatic tracking deviates from a feature point. If the tracking deviates, the operator presses the "Stop" button on the input device 5. When the operator presses the "Stop" button, the key image selection unit 7 adds, as a key image, the image displayed at this point of time or an image located forward from the image by a predetermined number of images. The apparatus displays the added key image to prompt the operator to designate a feature point.

This technique can minimize the feature point designation operation required for the operator. If a good tracking result is obtained, only two images are required. If a tracking result is poor, high image quality can be ensured by adding images.

(Fourth Technique for Key Image Selection Processing)

This technique also adds key images when a tracking result is not good.

Figure 12:
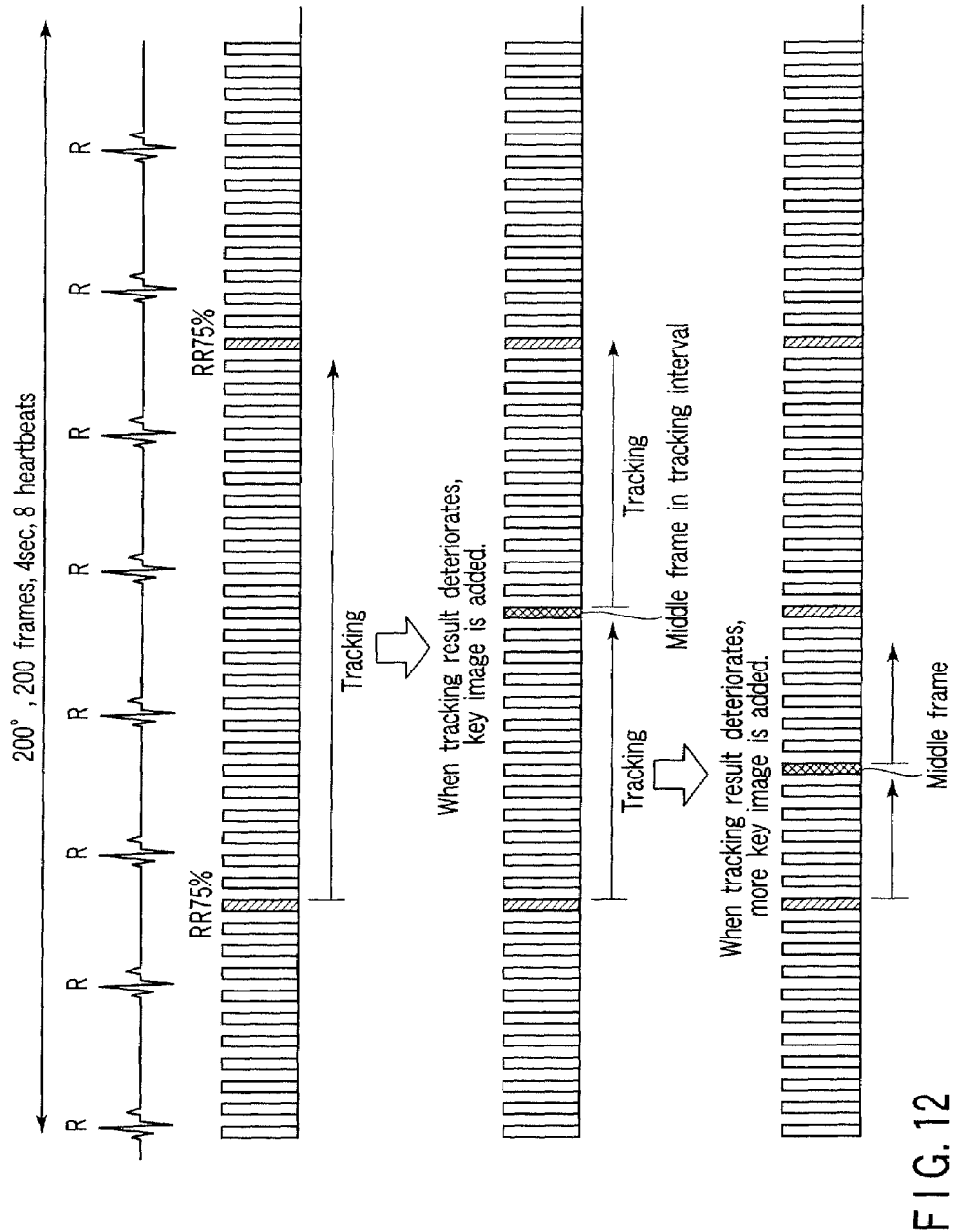
FIG. 12 is a supplementary view for explaining a fourth technique for the key image selection processing in step S2 in FIG. 4.

This technique selects, as key images, a pair of images which are located at the same cardiac phase and have a radiography angle difference of about 90°. The operator designates feature points on this pair of key images. As shown in FIG. 12, the apparatus then performs tracking processing with the feature points designated on the key images being base points. If the tracking processing 11 determines that a tracking result is not good, the key image selection unit 7 adds, as a key image, an image located substantially in the middle between the pair of key images. The apparatus repeats this operation.

Note that this apparatus uses one of the following methods as a method of determining whether a tracking result is good.

(1) Monitoring Correlation Values

The following will exemplify a case wherein a cross-correlation technique is used as a tracking technique. In this case, if a good correlation is obtained between images, the correlation value becomes high. If a good correlation cannot be obtained between images due to, for example, the overlapping of another object on the background, the correlation value becomes small. Therefore, the tracking processing unit 11 monitors correlation values. While high correlation values are maintained, it is determined that good tracking is performed. If a small correlation value is obtained, it is determined that the tracking result is poor.

(2) Monitoring Product of Correlation Values

The tracking processing unit 11 monitors the product of the above correlation values. Let $C_i$ be the correlation value between a image i and a image i+1. Assume that in this case, the correlation value $C_i$ is a normalized value, and satisfies $0 < C_i < 1$. Assume then that $S = \Sigma(1 - C_i)$. This technique monitors S. If S becomes a predetermined value or more, it is determined that the tracking result is poor.

(3) Tracking is sequentially done from key image N to key image N+1. The distance from a feature point designated on the key image N+1 to a feature point tracked on key image N+1 is measured. It is selected that the tracking result is good when the distance is shorter than the predetermined values, and is selected that the tracking result is bad when the distance is longer than the predetermined value.

(Fifth Technique for Key Image Selection Processing)

Figure 13:
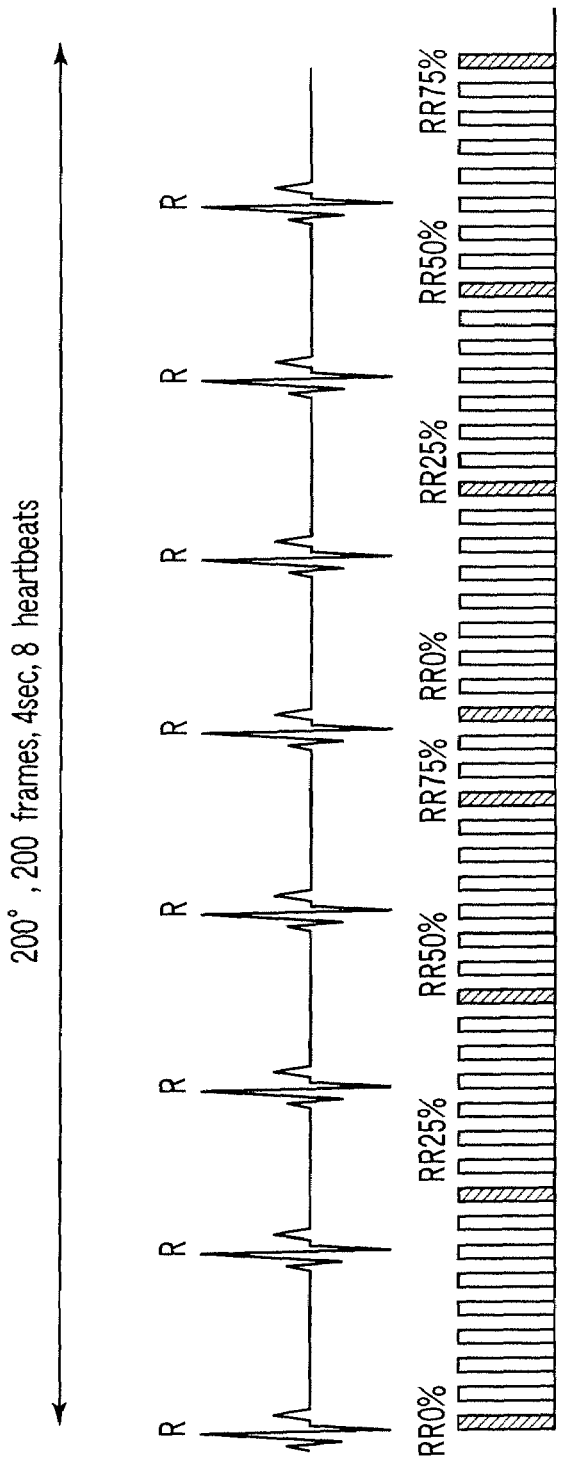
FIG. 13 is a supplementary view for explaining a fifth technique for the key image selection processing in step S2 in FIG. 4.

This technique sequentially selects shifted cardiac phases. Images at different cardiac phases are automatically selected as key images at a rate of one image per heartbeat. As shown in FIG. 13, for example, this apparatus selects a image at a cardiac phase of 0% (RR0%) from the first heartbeat. The apparatus selects a image at RR25% from the second heartbeat. The apparatus selects a image at RR50% from the third heartbeat. The apparatus selects a image at RR75% from the fourth heartbeat. The apparatus selects a image at RR0% from the fifth heartbeat. The apparatus selects a image at RR25% from the sixth heartbeat. The apparatus selects a image at RR50% from the seventh heartbeat. The apparatus selects a image at RR75% from the eighth heartbeat.

With this operation, eight images are automatically selected from 200 images. The apparatus sequentially displays the eight images obtained in this manner on the monitor to prompt the operator to input feature points.

Cardiac phases as selection targets are preset in advance. At least two cardiac phases of the preset cardiac phases as selection targets are set to be equivalent.

According to this technique, since two images are selected at each of the phases RR0%, RR25%, RR50%, and RR75%, the three dimensional coordinates of feature points can be calculated by using four phases. This apparatus generates four reconstructed images at RR0%, RR25%, RR50%, and RR75%. Sequentially switching and displaying the four reconstructed images allow to observe images which make the observer feel as if the heart was moving.

(First Modification)

Figure 14:
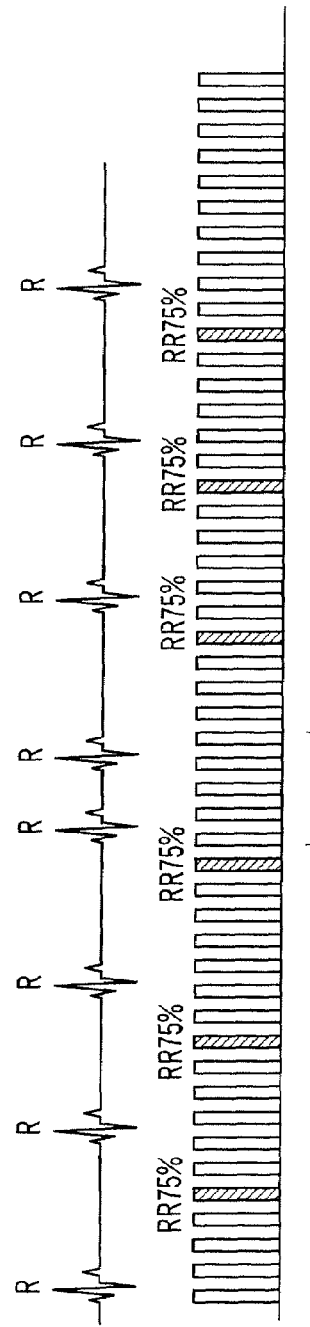
FIG. 14 is a view showing a modification of this embodiment.

If arrhythmia has occurred as shown in FIG. 14, no images are automatically selected from the corresponding heartbeat. In a heartbeat with arrhythmia, since the movement of the heart is not steady, it is difficult for the operator to designate a feature point. In order to save the operator from performing difficult operation, therefore, the apparatus does not automatically select any images with arrhythmia. When determining the presence of arrhythmia, the apparatus monitors heart rates (RR intervals), and determines a heartbeat accompanying an abrupt decrease or increase in RR interval by using a threshold.

Figure 15:
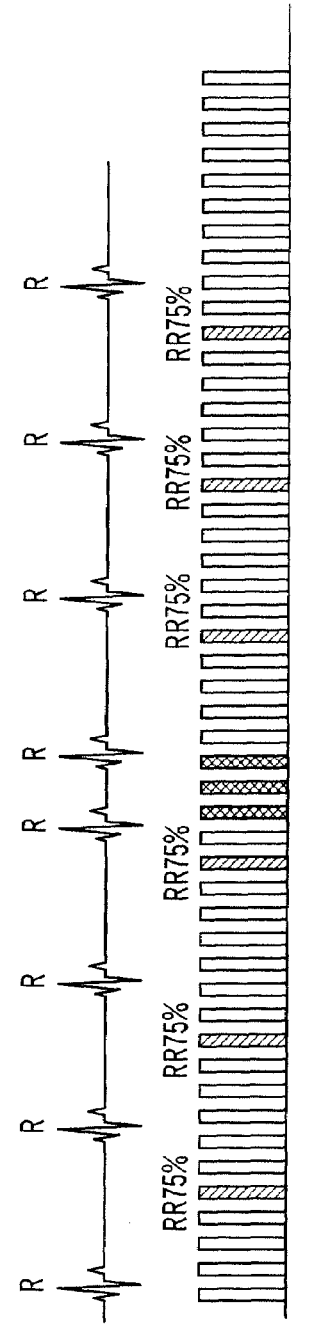
FIG. 15 is a view showing a modification of this embodiment.

In addition, when arrhythmia occurred as shown in FIG. 15, it suffices to automatically select many images in the corresponding heartbeat. In a heartbeat with arrhythmia, since the movement of the heart is not steady, the tracking performance deteriorates. Therefore, prompting the operator to input feature points in many images will stabilize the tracking performance and image quality.

(Second Modification)

Key images are stably and automatically selected by the first to fifth techniques described above. Each technique further includes a function of allowing the operator to change an automatically selected key image at his/her own discretion. Assume that image #34 is automatically selected as a key image by one of the first to fifth techniques. The key image of image #34 is displayed on the screen to prompt the operator to select a feature point. When, however, the operator operates the "→" mark displayed on an end of the screen or the "→" key on the keyboard at his/her own discretion, image #35 adjacent to the automatically selected key image is set as a new key image. The operator can designate a feature point on image #35.

If, for example, a feature point overlaps a blood vessel on an automatically selected key image, it is difficult for the operator to identify the feature point. In such a case, it is possible to change (replace) the automatically selected key image to an adjacent image in which the feature point does not overlap the blood vessel.

In addition, the operator adds neighboring image #35 to the key images by using the "add →" mark displayed in the window or the "ctrl"+"→" key of the keyboard.

If, for example, a feature point overlaps a blood vessel on an automatically selected key image, it is difficult for the operator to identify the feature point, and the tracking accuracy deteriorates in the neighboring image. In such a case, it is possible to add a image adjacent to the automatically selected key image to the key images. This makes it possible to stabilize the tracking accuracy.

Assume that the operator is permitted to perform manual fine adjustment. In this case, even if all selected key images are collected, there is a possibility that the minimum necessary condition of this function, i.e., "at least two images of selected key images should be at the same cardiac phase", is not satisfied. For this reason, one of the following techniques is added.

There is provided a technique characterized in that if there are not two or more images at preset cardiac phases when the operator finally checks all images on which feature points have been designated after automatic selection or "automatic selection+manual fine adjustment", images at the same cardiac phase are additionally and automatically selected and the operator is prompted to input feature points.

There is provided a technique characterized in that it has an interface so that if there are not two or more images at preset cardiac phases and there are two or more images with the same cardiac phase at other cardiac phases when the operator finally checks all images on which feature points have been designated after automatic selection and manual fine adjustment, the interface asks the operator whether to perform reconstruction processing at the same cardiac phase.

There is provided a technique characterized in that if there are not two or more images at preset cardiac phases and there are two or more images with the same cardiac phase at other cardiac phases when the operator finally checks all images on which feature points have been designated after automatic selection and manual fine adjustment, reconstruction processing is performed at the same cardiac phase.

(Third Modification)

When no R wave can be detected in an electrocardiogram of a subject to be examined or R-R intervals extremely vary, the key image selection unit 7 discards an initially automatically selected key image, and forcibly selects key images at equal time intervals regardless of cardiac phases. Alternately, the key image selection unit 7 discards an initially automatically selected key image and prompts the operator to manually designate a key image.

(Fourth Modification)

The key image selection unit 7 adds images at both ends of a set of images as initially automatically selected key images in the first to fifth techniques, i.e., adds images acquired first and last as key images. This operation is performed to track all the acquired images. This makes it possible to track in an interval from an image at one end to an initially automatically selected key image.

There is provided a technique characterized in that if there are not two or more images at preset cardiac phases and there are two images or more at the same cardiac phase when the operator finally checks all images on which feature points have been designated after automatic selection or "automatic selection+manual fine adjustment", reconstruction processing is performed at the cardiac phase.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A three dimensional image processing apparatus comprising:
   a storage unit which stores data of a plurality of images in different radiographing directions together with information concerning cardiac phases;
   a key image selection unit which selects a plurality of key images from said plurality of images;
   a feature point designation unit which designates feature points on the selected key images in accordance with operation by an operator; and
   an image reconstruction unit which reconstructs a three dimensional image from said plurality of images on the basis of positions of the designated feature points,
   wherein the key image selection unit selects, as the key images, a pair of images which are located at the same cardiac phase and whose radiographing directions are different by a substantially predetermined angle and a plurality of images spaced apart from each other by an angle obtained by substantially equally dividing an interval between the pair of images by a predetermined number.

2. An apparatus according to claim 1, wherein the key image selection unit selects the pair of images whose radiographing directions are different by a substantially 90°.

3. An apparatus according to claim 1, wherein the key image selection unit selects the pair of images which are located at the same cardiac phase and whose radiographing directions whose difference is nearest to 90°.

4. An apparatus according to claim 1, wherein the image reconstruction unit includes
   a three dimensional position calculation unit which calculates three dimensional positions of the feature points on the basis of the radiographing directions of the key images and positions of the designated feature points in the key images,
   a re-projection position calculation unit which calculates positions of the feature points in said plurality of images, respectively, on the basis of the calculated three dimensional positions of the feature points and the radiographing directions of said plurality of images,
   a feature point tracking unit which tracks the feature points on said plurality of images with a feature point designated on said each key image being a base point,
   a positional shift calculation unit which calculates a positional shift between the position of the reprojected feature point and a position of the tracked feature point for each of said plurality of images,
   a position correction unit which corrects the positions of said plurality of images on the basis of the calculated positional shifts, and an image reconstruction unit which reconstructs the three dimensional image on the basis of said plurality of corrected images and the radiographing directions.

5. A three dimensional image processing apparatus comprising:
- a storage unit which stores data of a plurality of images in different radiographing directions together with information concerning cardiac phases;
- a key image selection unit which selects a plurality of key images from said plurality of images;
- a feature point designation unit which designates feature points on the selected key images in accordance with operation by an operator; and
- an image reconstruction unit which reconstructs a three dimensional image from said plurality of images on the basis of positions of the designated feature points,
- wherein the key image selection unit selects the key images at a rate of two images per heartbeat when a heart rate is not more than a first threshold, and selects the key images at a rate of one image per heartbeat when a heart rate is higher than the first threshold.

6. An apparatus according to claim 5, wherein the image reconstruction unit includes
- a three dimensional position calculation unit which calculates three dimensional positions of the feature points on the basis of the radiographing directions of the key images and positions of the designated feature points in the key images,
- a re-projection position calculation unit which calculates positions of the feature points within images on said plurality of images, respectively, on the basis of the calculated three dimensional positions of the feature points and the radiographing directions of said plurality of images,
- a feature point tracking unit which tracks the feature points on said plurality of images with a feature point designated on said each key image being a base point,
- a positional shift calculation unit which calculates a positional shift between the calculated position of the feature point and a position of the tracked feature point for each of said plurality of images,
- a position correction unit which corrects the positions of said plurality of images on the basis of the calculated positional shifts, and
- an image reconstruction unit which reconstructs the three dimensional image on the basis of said plurality of corrected images and the radiographing directions.

7. An apparatus according to claim 5, wherein the key image selection unit selects images at the same cardiac phase as the key images.

8. An apparatus according to claim 5, wherein the first threshold is an any value within the range of 60-80.

9. An apparatus according to claim 5, wherein the key image selection unit selects the key images at a rate of one image per heartbeat when a heart rate is higher than the first threshold and not more than a second threshold, and selects the key images at a rate of one image per two heartbeats when a heart rate is higher than the second threshold.

10. An apparatus according to claim 9, wherein the first threshold is an any value within the range of 60-80 and the second threshold is an any value within the range of 120-150.

11. An apparatus according to claim 9, wherein the second threshold is an any value within the range of 120-150.

12. A three dimensional image processing apparatus comprising:
- a storage unit which stores data of a plurality of images in different radiographing directions together with information concerning cardiac phases;
- a key image selection unit which selects a plurality of key images from said plurality of images;
- a feature point designation unit which designates feature points on the selected key images in accordance with operation by an operator; and
- an image reconstruction unit which reconstructs a three dimensional image from said plurality of images on the basis of positions of the designated feature points,
- wherein the key image selection unit selects the key images so that a ratio of image number of the selected key images to a heartbeat number when frequency of heartbeats are higher than a first threshold is lower than the ratio when frequency of heartbeats are not higher than the first threshold.

13. A three dimensional image processing apparatus comprising:
- a storage unit which stores data of a plurality of images in different radiographing directions together with information concerning cardiac phases;
- a key image selection unit which selects a plurality of key images from said plurality of images;
- a feature point designation unit which designates feature points on the selected key images in accordance with operation by an operator; and
- an image reconstruction unit which reconstructs a three dimensional image from said plurality of images on the basis of positions of the designated feature points,
- wherein the key image selection unit selects the key images at a rate of one image per heartbeat when a heart beat is not more than a first threshold, and selects the key images at a rate of one image per heart beats when a heart rate is more than the first threshold.

14. A three dimensional image processing apparatus comprising:
- a storage unit which stores data of a plurality of images in different radiographing directions together with information concerning cardiac phases;
- a key image selection unit which selects a plurality of key images from said plurality of images;
- a feature point designation unit which designates feature points on the selected key images in accordance with operation by an operator; and
- an image reconstruction unit which reconstructs a three dimensional image from said plurality of images on the basis of positions of the designated feature points,
- wherein the key image selection unit selects the key images at a rate of two images per heartbeat when an acquisition period of said plurality of images is not more than a first heart rate, and selects the key images at a rate of one image per heartbeat when an acquisition period of said plurality of images is higher than the first heart rate.

15. An apparatus according to claim 14, wherein the image reconstruction unit includes
- a three dimensional position calculation unit which calculates three dimensional positions of the feature points on the basis of the radiographing directions of the key images and positions of the designated feature points in the key images,
- a re-projection position calculation unit which calculates positions of the feature points within images on said plurality of images, respectively, on the basis of the calculated three dimensional positions of the feature points and the radiographing directions of said plurality of images, a feature point tracking unit which tracks the feature points on said plurality of images with a feature point designated on said each key image being a base point, a positional shift calculation unit which calculates a positional shift between the calculated position of the feature point and a position of the tracked feature point for each of said plurality of images, a position correction unit which corrects the positions of said plurality of images on the basis of the calculated positional shifts, and an image reconstruction unit which reconstructs the three dimensional image on the basis of said plurality of corrected images and the radiographing directions.

16. An apparatus according to claim 14, wherein the key image selection unit selects images at the same cardiac phase as the key images.

17. An apparatus according to claim 14, wherein the first heart rate is an any value within the range of 2-5.

18. An apparatus according to claim 14, wherein the key image selection unit selects the key images at a rate of one image per heartbeat when an acquisition period of said plurality of images is higher than the first heart rate and not more than a second heart rate, and selects the key images at a rate of one image per two heartbeats when an acquisition period of said plurality of images is higher than the second heart rate.

19. An apparatus according to claim 18, wherein the first heart rate is an any value within the range of 2-5 and the second heart rate is an any value within the range of 10-15.

20. A three dimensional image processing apparatus comprising:

a storage unit which stores data of a plurality of images in different radiographing directions together with information concerning cardiac phases;

a key image selection unit which selects a plurality of key images from said plurality of images;

a feature point designation unit which designates feature points on the selected key images in accordance with operation by an operator; and an image reconstruction unit which reconstructs a three dimensional image from said plurality of images on the basis of positions of the designated feature points, wherein the key image selection unit selects the key images at a rate of one image per heartbeat when an acquisition period of said plurality of images is not more than a first heart rate, and selects the key images at a rate of one image per two heartbeats when an acquisition period of said plurality of images is higher than the first heart rate.

21. A three dimensional image processing apparatus comprising:

a storage unit which stores data of a plurality of images in different radiographing directions together with information concerning cardiac phases;

a key image selection unit which selects a plurality of key images from said plurality of images;

a feature point designation unit which designates feature points on the selected key images in accordance with operation by an operator; and an image reconstruction unit which reconstructs a three dimensional image from said plurality of images on the basis of positions of the designated feature points, wherein the key image selection unit selects the key images so that a ratio of image number of the selected key images to a heartbeat number when an acquisition period of said plurality of images is not more than a predetermined heart rate is lower than the ratio when the acquisition period is higher than the predetermined heart rate.

22. A three dimensional image processing apparatus comprising:

a storage unit which stores data of a plurality of images in different radiographing directions together with information concerning cardiac phases;

a key image selection unit which selects a plurality of keys image from said plurality of images;

a feature point designation unit which designates feature points on the selected key images in accordance with operation by an operator;

a feature point tracking unit which tracks the feature points on said plurality of images with a feature point designated on said each key image being a base point, a display unit which displays positions of the tracked feature points on said plurality of images;

an image reconstruction unit which reconstructs a three dimensional image from said plurality of images on the basis of positions of the designated feature points and positions of the tracked feature points; and an input unit which inputs a command to add an arbitrary image between the selected key images as a new key image.

23. An apparatus according to claim 22, wherein the image reconstruction unit includes a three dimensional position calculation unit which calculates three dimensional positions of the feature points on the basis of the radiographing directions of the key images and positions of the designated feature points in the key images, a re-projection position calculation unit which calculates positions of the feature points within images on said plurality of images, respectively, on the basis of the calculated three dimensional positions of the feature points and the radiographing directions of said plurality of images, a feature point tracking unit which tracks the feature points on said plurality of images with a feature point designated on said each key image being a base point, a positional shift calculation unit which calculates a positional shift between the calculated position of the feature point and a position of the tracked feature point for each of said plurality of images, a position correction unit which corrects the positions of said plurality of images on the basis of the calculated positional shifts, and an image reconstruction unit which reconstructs the three dimensional image on the basis of said plurality of corrected images and the radiographing directions.

24. An apparatus according to claim 22, wherein the feature point tracking unit tracks the feature points on said plurality of images with a feature point on the added new key image being a base point.

25. An apparatus according to claim 22, wherein an intermediate image between the selected key images is added as a new key image.

26. A three dimensional image processing apparatus comprising:

a storage unit which stores data of a plurality of images in different radiographing directions together with information concerning cardiac phases;

a key image selection unit which selects a plurality of key images from said plurality of images;

a feature point designation unit which designates feature points on the selected key images in accordance with operation by an operator;

a feature point tracking unit which tracks the feature points on said plurality of images with a feature point designated on said each key image being a base point, a determination unit which determines a quality of the tracking result;

a key image addition unit which adds an intermediate image between the selected key images as a new key image when the tracking result is relatively low; and an image reconstruction unit which reconstructs a three dimensional image from said plurality of images on the basis of positions of the designated feature points and positions of the tracked feature points.

27. An apparatus according to claim 26, wherein the image reconstruction unit includes a three dimensional position calculation unit which calculates three dimensional positions of the feature points on the basis of the radiographing directions of the key images and positions of the designated feature points in the key images, a re-projection position calculation unit which calculates positions of the feature points within images on said plurality of images, respectively, on the basis of the calculated three dimensional positions of the feature points and the radiographing directions of said plurality of images, a feature point tracking unit which tracks the feature points on said plurality of images with a feature point designated on said each key image being a base point, a positional shift calculation unit which calculates a positional shift between the calculated position of the feature point and a position of the tracked feature point for each of said plurality of images, a position correction unit which corrects the positions of said plurality of images on the basis of the calculated positional shifts, and an image reconstruction unit which reconstructs the three dimensional image on the basis of said plurality of corrected images and the radiographing directions.

28. An apparatus according to claim 26, wherein the feature point tracking unit tracks the feature points on said plurality of images with a feature point on the added new key image being a base point.

29. A three dimensional image processing apparatus comprising:

a storage unit which stores data of a plurality of images in different radiographing directions together with information concerning cardiac phases;

a key image selection unit which selects a plurality of key images from said plurality of images;

a feature point designation unit which designates feature points on the selected key images in accordance with operation by an operator;

a feature point tracking unit which tracks the feature points on said plurality of images with a feature point designated on said each key image being a base point, and an image reconstruction unit which reconstructs a three dimensional image from said plurality of images on the basis of positions of the designated feature points and positions of the tracked feature points, wherein the key image selection unit selects the key images from a plurality of images in heart beat periods other than arrhythmia.

30. A three dimensional image processing apparatus comprising:

a storage unit which stores data of a plurality of images in different radiographing directions together with information concerning cardiac phases;

a key image selection unit which selects a plurality of key images from said plurality of images;

a key image changing unit which changes the selected key image for other key image under a manual operation;

a feature point designation unit which designates feature points on the selected/changed key images in accordance with operation by an operator;

a feature point tracking unit which tracks the feature points on said plurality of images with a feature point designated on said each key image being a base point, and an image reconstruction unit which reconstructs a three dimensional image from said plurality of images on the basis of positions of the designated feature points and positions of the tracked feature points.

* * * * *